United States Patent [19]

Altman et al.

[11] Patent Number: 5,658,327
[45] Date of Patent: Aug. 19, 1997

[54] INTRACARDIAC LEAD HAVING A COMPLIANT FIXATION DEVICE

[75] Inventors: Peter A. Altman, San Francisco; M. Elizabeth Bush, Fremont; Dean F. Carson, Mountain View, all of Calif.

[73] Assignee: Ventritex, Inc., Sunnyvale, Calif.

[21] Appl. No.: 574,801

[22] Filed: Dec. 19, 1995

[51] Int. Cl.$^6$ ...................................................... A61N 1/05
[52] U.S. Cl. ............................................................. 607/127
[58] Field of Search ................................... 607/119, 122, 607/126, 127, 128, 130, 131; 128/642

[56] References Cited

U.S. PATENT DOCUMENTS

| | | | |
|---|---|---|---|
| 4,000,745 | 1/1977 | Goldberg | 607/127 |
| 4,106,512 | 8/1978 | Bisping . | |
| 4,136,702 | 1/1979 | Trabucco | 607/130 |
| 4,144,890 | 3/1979 | Hess | 607/130 |
| 4,233,992 | 11/1980 | Bisping . | |
| 4,235,246 | 11/1980 | Weiss | 607/131 |
| 4,282,885 | 8/1981 | Bisping . | |
| 4,649,938 | 3/1987 | McArthur . | |
| 4,827,940 | 5/1989 | Mayer et al. | 128/642 |
| 4,858,623 | 8/1989 | Bradshaw et al. . | |
| 5,003,992 | 4/1991 | Holleman et al. . | |
| 5,152,299 | 10/1992 | Soukup . | |
| 5,246,014 | 9/1993 | Williams et al. | 607/122 |
| 5,300,108 | 4/1994 | Rebell et al. | 607/127 |
| 5,344,439 | 9/1994 | Otten | 607/126 |
| 5,431,681 | 7/1995 | Helland | 607/119 |
| 5,522,876 | 6/1996 | Rusink | 607/122 |
| 5,542,173 | 8/1996 | Mar et al. | 607/119 |

*Primary Examiner*—William E. Kamm
*Assistant Examiner*—George R. Evanisko
*Attorney, Agent, or Firm*—Steven M. Mitchell; M. Elizabeth Bush; Mark J. Meltzer

[57] ABSTRACT

Intracardiac lead for compliant fixation of a distal end of the lead to cardiac tissue. A fixation helix is disposed at the distal end of the lead. The fixation helix has a first end rigidly attached to the compliant fixation device and a second end that is sharpened to facilitate insertion of the fixation helix into cardiac tissue. The fixation helix can be designed to provide for either electrically active or inactive fixation. Once the lead is implanted in the cardiac tissue, the compliant fixation device, connecting the lead with the fixation helix, reduces the amount of lead movement that is transferred to the patient's tissue at the site of implantation of the fixation helix and reduces those forces from lead movement that could cause dislodgment of the fixation helix. The compliant fixation device thereby decreases the amount of irritation to the cardiac tissue, lessens the possibility of fibrous tissue growth around the area of the fixation helix, decreases the chance of dislodgment of the fixation helix, and reduces the possibility of perforation of the cardiac wall or tamponade of the pericardial sac.

11 Claims, 7 Drawing Sheets

INTRACARDIAC LEAD HAVING A COMPLIANT FIXATION DEVICE

BACKGROUND OF THE INVENTION

1. Field of the Invention

The present invention relates to an apparatus for flexibly attaching a medical device to human tissue. In particular, the apparatus is used to flexibly secure the distal end of a defibrillation, sensing or pacing lead to cardiac tissue.

2. Related Art

Cardiac sensing and stimulation leads generally have a lead body forming a tube, an electrode tip located at the distal end of the lead body, and a flexible insulated conductor traversing the length of the lead body for carrying signals and stimulating pulses between the electrode tip and a cardiac stimulating or sensing device, such as a pacemaker, defibrillator or sensor. To best sense electrical signals from the heart or to stimulate the heart, the electrode tip must be maintained in contact with the cardiac tissue to be sensed or stimulated.

Typically, cardiac leads are inserted into the heart through the superior vena cava. The lead is then guided through the right atrium and into the right ventricle of the heart. The electrode tip is then secured to the cardiac tissue at the apex of the right ventricle or other portion of the heart such as the septum or atrium. There are a variety of known ways to maintain the electrode tip in contact with the cardiac tissue to be stimulated. One common method is to use tines to secure the electrode tip to the cardiac tissue. A second common method is to attach a sharpened fixation helix (i.e., a screw) to the distal end of the electrode tip. The fixation helix is then rotated and screwed into the cardiac tissue to be stimulated. The tines are a form of mechanically "passive" fixation, and the helix is a form of mechanically "active" fixation.

Fixation means are generally referred to as being either electrically active or electrically inactive. In the case of electrically active fixation, the fixation helix doubles as the electrode tip because the fixation helix is electrically connected via a conductor to the cardiac stimulating or sensing device. Thus, an electrically active fixation helix secures the lead to the cardiac tissue to be sensed or stimulated and also provides sensing or cardiac stimulation to the tissue.

In the case of electrically inactive fixation, the fixation helix is not electrically connected to the cardiac sensing or stimulating device. Instead, a separate electrode is affixed to the distal end of the lead body. A wire conductor in the insulated sheath electrically connects the electrode tip to the cardiac stimulating or sensing device. The fixation helix is used only to secure the electrode tip to the cardiac tissue to be sensed or stimulated, but the helix does not actually carry electrical current.

Several conventional methods have been used to attach the fixation helix to the cardiac tissue. In one implementation of the helix, the lead body is fixedly attached to the fixation helix. When the lead body is rotated, the fixation helix also rotates. Thus, the helix can be screwed into the cardiac tissue by rotating the body of the lead to which it is attached. In a second implementation of the helix, it is rotatably attached to the end of the lead so that it can turn freely with respect to the lead. To screw the helix into the cardiac tissue, a stylet having a screwdriver tip is inserted into the lead. The screwdriver tip of the stylet fits into a slot on the back side of the fixation helix for screwing the helix into place. In a third implementation of the helix, a conductor coil is used to rotate the fixation helix within the lead. The fixation helix is connected to the end of the coiled conductor. Thus, when the coiled conductor is rotated, the fixation helix also rotates.

The use of a sharpened fixation helix as a fixation device has a drawback. During insertion of the lead into the heart cavity, the sharpened end of the fixation helix may snag adjacent cardiac tissue. Thus, some conventional leads are made such that, during insertion of the lead into the heart cavity, the fixation helix is retracted into the lead body. Once the lead has been inserted into the heart cavity, a stylet is inserted into the lead body and is used to deploy the fixation helix for insertion into the cardiac tissue. The fixation helix is then screwed into the cardiac tissue by rotation of the entire lead body.

One problem common to all of the devices described above that use a conventional fixation helix is that the distal end of the lead body is relatively stiff due to the bulky housing of the lead body. Because the fixation helix itself is also rigid and forms an additional extension from the housing, the length and stiffness of the distal end of the lead body is further increased when the fixation helix is extended. After insertion into the cardiac tissue, the fixation helix is kept fixed, in a linear alignment, in relation to the lead body. This stiff, linear orientation allows for leverage forces from the lead to be transferred to the embedded fixation helix. Movement of the inserted fixation helix can result in damage and irritation to the cardiac tissue at the site of attachment. Typical heart wall motion or body motion, such as movement of limbs, may also cause the lead to exert forces on the fixation helix, which may cause irritation or inflammation of the cardiac tissue, or perforation of the heart wall.

Damaged or irritated areas of cardiac tissue often lead to the development of scar tissue or increased fibrous growth due to continuous inflammation. The presence of scar tissue at the site of the electrode changes the sensing characteristics of the lead due to the impedance of the scar tissue and may result in lead failure or may require additional stimulation to the cardiac tissue. Additional stimulation may result in a rapid decrease in the life of the battery used as the energy source for the cardiac stimulating device. Further, the presence of increased fibrous growth may result in increased difficulty of lead extraction.

Thus, an apparatus is needed that reduces the forces on the fixation helix after implantation so that lead movement will not cause movement of the fixation helix within the tissue.

SUMMARY OF THE INVENTION

The present invention provides a compliant fixation device for connecting a fixation helix to the distal end of a pacing or defibrillation lead. In each of the embodiments shown, a rigid torque transmission means is shown for enabling the user to rotate the fixation helix to implant the helix in a patient's cardiac tissue. The fixation helix can be designed in these embodiments to provide either an electrically active or inactive fixation. Once the fixation helix is implanted, the flexible qualities of the present invention minimize the moment that the lead body can apply at the site of fixation. Thus, movements of the lead are not transferred directly to the cardiac tissue surrounding the fixation helix. This reduces mechanical trauma to cardiac tissue and thereby decreases inflammation and fibrous growth around the fixation site.

In the preferred embodiment, the compliant fixation device includes a spring that connects a fixation helix to a distal end of a lead. The spring may be surrounded by a biocompatible, bioreactive material. This material maintains the spring in a rigid state for efficient torque transmission during implantation of the fixation helix. Once the material comes in contact with the patient's blood, the material "bioreacts" by either dissolving in the blood or reacting to the blood such that it softens and expands. This allows the spring to bend and flex freely, thereby absorbing movements of the lead and preventing movement from being directly transferred to the cardiac tissue surrounding the fixation helix.

In each of the other embodiments presented herein, a connector in a compliant fixation device connects the distal end of a lead to a fixation helix to decouple movement of the lead from the fixation helix after implantation. Thus, the present invention allows for efficient implantation of the fixation helix while reducing harm to the cardiac tissue after implantation.

BRIEF DESCRIPTION OF THE FIGURES

The foregoing and other features and advantages of the invention will be apparent from the following, more particular description of a preferred embodiment of the invention, as illustrated in the accompanying drawings.

DETAILED DESCRIPTION OF THE PREFERRED EMBODIMENTS

A preferred embodiment of the present invention is now described with reference to the figures where like reference numbers indicate identical or functionally similar elements. Also in the figures, the left most digit of each reference number corresponds to the figure in which the reference number is first used. While specific configurations and arrangements are discussed, it should be understood that this is done for illustrative purposes only. A person skilled in the relevant art will recognize that other configurations and arrangements can be used without departing from the spirit and scope of the invention. It will be apparent to a person skilled in the relevant art that this invention can also be employed in a variety of other devices and applications.

Figure 1:
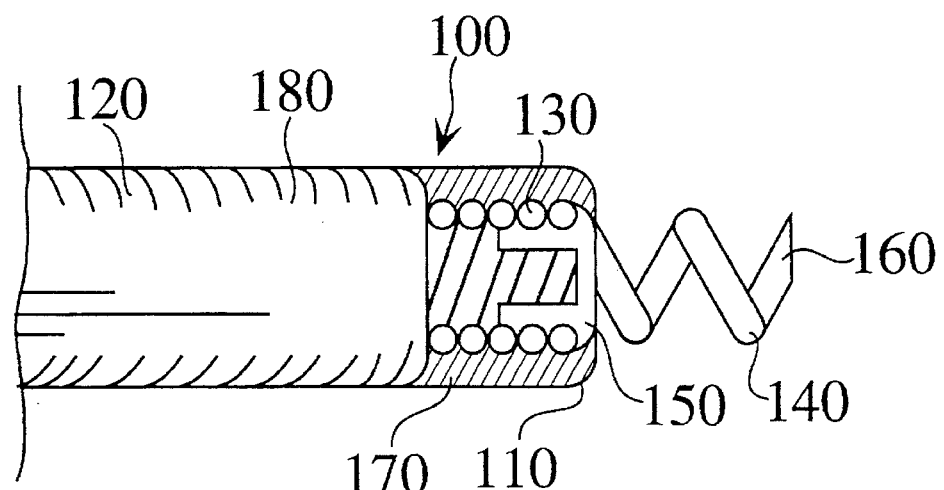
FIG. 1 is a partially sectional view of a lead 100 of the preferred embodiment.
Figure 2:
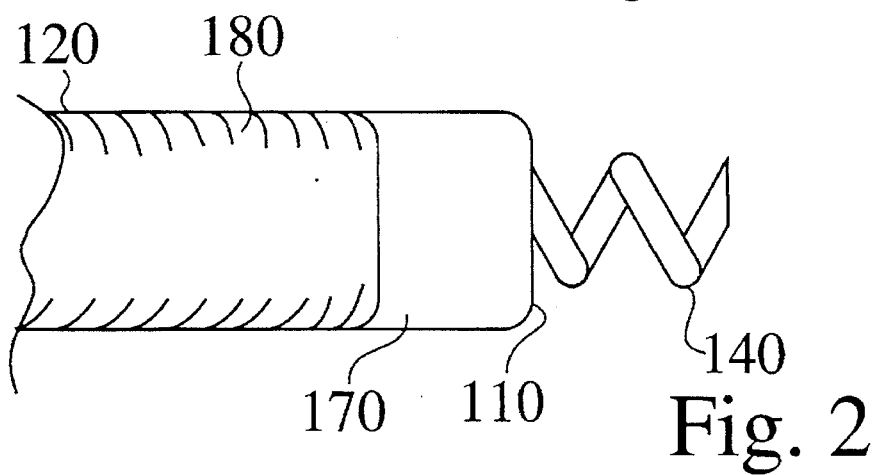
FIG. 2 is an exterior view of the lead of FIG. 1.
Figure 3:
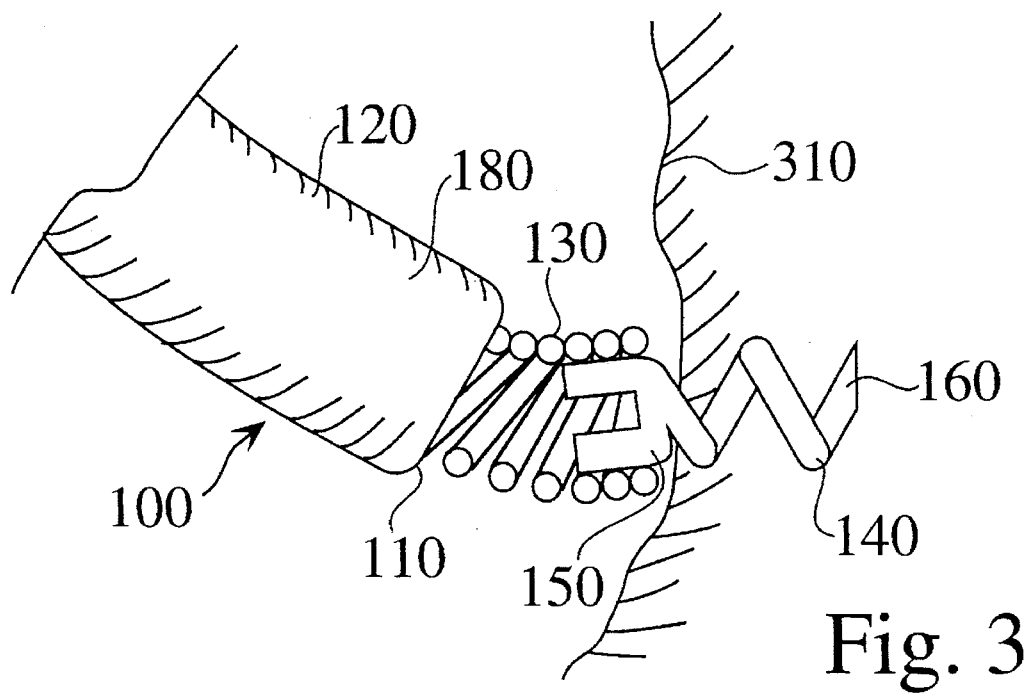
FIG. 3 is a partially sectional view of the lead of FIG. 1 after being implanted in cardiac tissue.

Referring to FIGS. 1-3, a distal end 110 of a lead 100 of the preferred embodiment is shown. Lead 100 has a lead body 120. Distal end 110 of lead 100 includes a spring or connector 130 and a fixation helix 140 having a first end 150 and a second end 160. First end 150 is slotted to receive a screwdriver stylet (not shown). The stylet is typically inserted into lead body 120 to aid in maneuvering distal end 110 into position inside a patient's heart. Once the stylet is inserted into lead body 120, the screwdriver tip fits into slotted first end 150 of fixation helix 140. As the stylet is rotated, the torque from the rotation of the stylet is transferred to fixation helix 140 via the meshing of the screwdriver tip and first end 150 to screw fixation helix 140 into a patient's cardiac tissue. Second end 160 of fixation helix 140 is sharpened to facilitate insertion into the cardiac tissue.

During implantation of lead 100 into the cardiac tissue, spring 130 is maintained in a rigid state by means of a bioreactive material 170. A bioreactive material dissolves or otherwise undergoes a physical change when it comes in contact with blood or other liquids. Material 170 surrounds spring 130 at distal end 110 of lead 100. Material 170 ensures that spring 130 remains substantially rigid during implantation to facilitate implantation of fixation helix 140 into the cardiac tissue. Material 170 may be made from a dissolvable material, such as mannitol (a blood soluble sugar) or polyethylene glycol (PEG), or any other biocompatible, bioreactive material. Any material used should remain in an undissolved state for a period long enough to allow implantation of fixation helix 140. Material 170 preferably should dissolve between 10 to 30 minutes after insertion of lead 100 into the heart cavity. However, any material that dissolves within 24 hours after insertion of lead 100 into the heart cavity is sufficient.

As an alternative embodiment, the spring 130 may be implanted without material 170 with the torque necessary for implantation being transmitted to the fixation helix 140 solely by a stylet. Conversely, if the material 170 is capable of transmitting a suitable torque for implantation, the lead may be implanted without use of a stylet. However, a stylet will probably be required for explant in most cases.

In a preferred alternate embodiment, material 170 is a hydrogel, such as polyethylene oxide (PEO). Typically, hydrogels remain a solid polymer during implantation of lead 100. Instead of dissolving after implantation, the hydrogel swells and softens upon contact with blood to provide flexibility around the area of the hydrogel. Ideally, a hydrogel that swells by two times its original volume may be used. This swelling and softening allows substantial flexible movement of distal end 110 of lead 100 after implantation and also prevents ingrowth of cardiac tissue from attaching to spring 130, thereby maintaining extractability of lead 100 should it need to be removed after chronic implant.

Lead 100 achieves electrically active fixation because spring 130 electrically connects fixation helix 140 to a cardiac stimulation device (e.g., a pacemaker or defibrillator). Spring 130 can be made from any fatigue resistant, biocompatible, electrically conductive material. In the preferred embodiment, spring 130 is made of a nickel-cobalt alloy, commonly referred to as MP35N wire, available from Fort Wayne Metals. Lead body 120 also includes an insulative sheath 180 that surrounds the coiled conductor. Insulative sheath 180 can be constructed from implantable polyurethane or silicone rubber or any other flexible, electrically insulating material that is biocompatible.

FIG. 3 shows lead 100 implanted into a patient's cardiac tissue 310. As shown in this embodiment, material 170 is dissolved so that spring 130 is allowed to freely bend and flex in response to forces on distal end 110 of lead 100 imparted by lead movement. Fixation helix 140 remains implanted in cardiac tissue 310 despite movements in lead 100.

It will be understood that the present invention can advantageously be used to affix a lead to other portions of the heart such as the intraventricular septum or to locations in the atrium.

Figure 4:
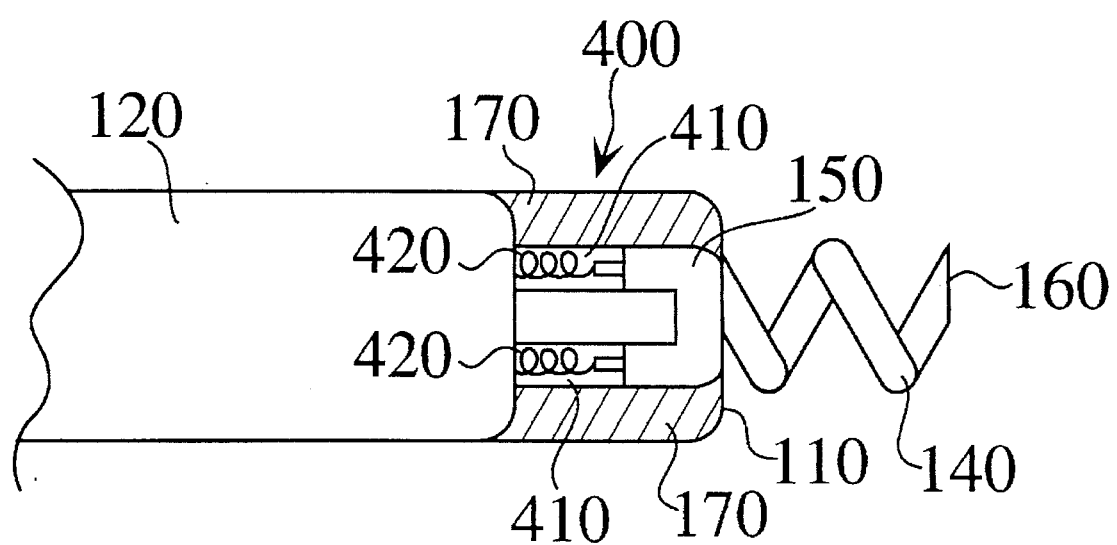
FIG. 4 is a partially sectional view of a second embodiment of a compliant fixation device of the present invention.

FIG. 4 shows a partially sectional view of a second embodiment of a compliant fixation device 400 of the present invention. A lead body 120 is shown having a distal end 110. A fixation helix 140 is disposed at distal end 110. Fixation helix 140 has a first end 150 which is slotted to receive a screwdriver stylet. A second end 160 of fixation helix 140 is sharpened to facilitate insertion of the helix into a patient's cardiac tissue. In this embodiment, the connectors are a pair of silicone rods 410 attached to first end 150 of fixation helix 140. As described above with respect to the preferred embodiment, silicone rods 410 are surrounded by a biocompatible, bioreactive material 170. Thus, after implantation, material 170 either dissolves or softens as described above. This allows the flexible silicone rods 410 to be free to compensate for lead movements.

This embodiment provides electrically active fixation because silicone rods 410 may contain coiled conductors 420 or cables (not shown) to provide an electrical connection to fixation helix 140 thereby achieving active fixation. As another alternative, silicone rods 410 may be loaded with carbon or metal powder to provide an electrical connection to fixation helix 140.

In an alternate embodiment, without coiled conductors 420, the embodiment would provide an electrically inactive fixation because silicone rods 410 would not provide an electrical connection between the power source and fixation helix 140. In this inactive embodiment, a wire connector (not shown) is inserted inside lead body 120 to electrically connect the cardiac stimulating or sensing device to the cardiac tissue.

Figure 5:
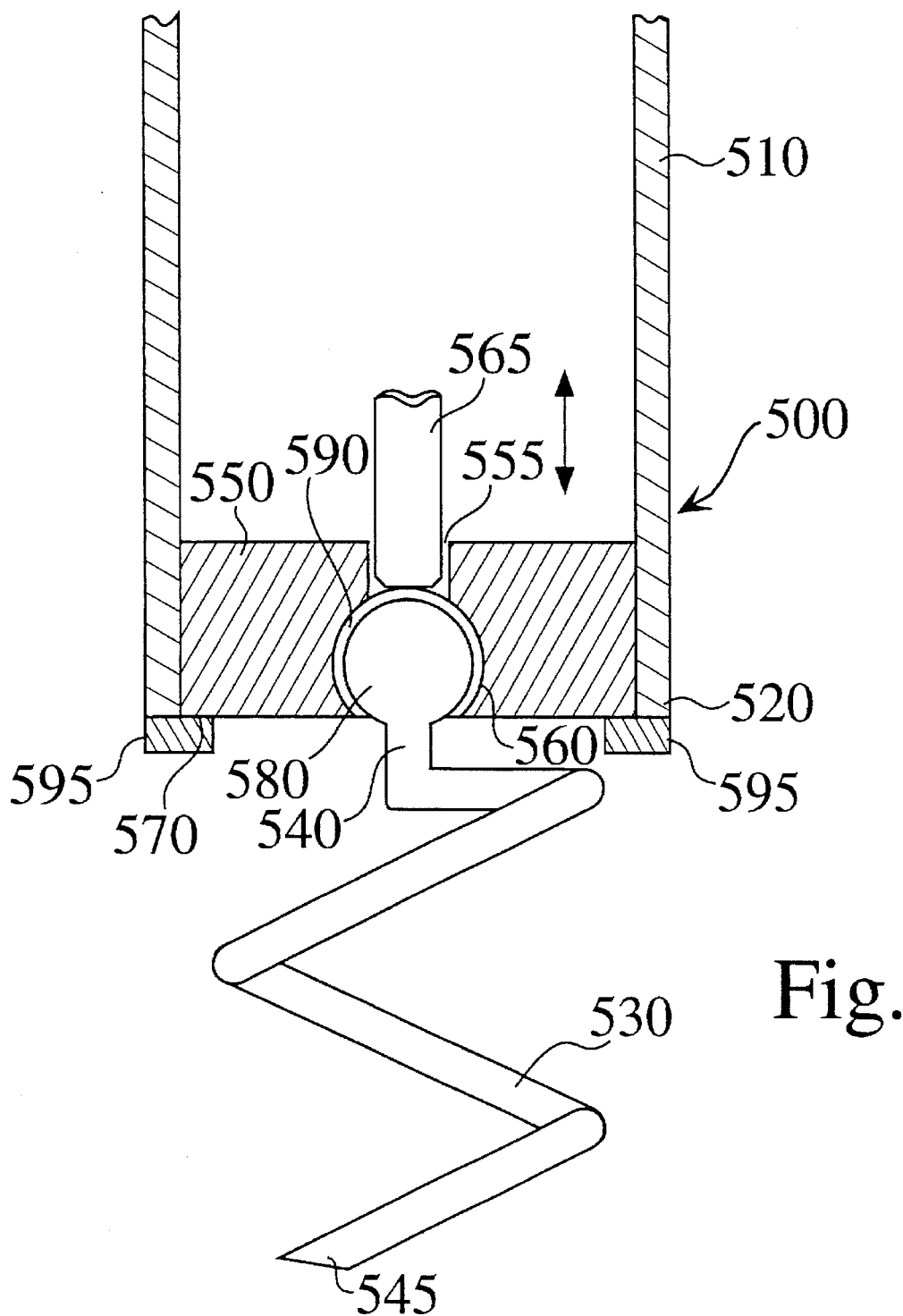
FIG. 5 is a sectional view of a third embodiment of a compliant fixation device of the present invention.

FIG. 5 shows a sectional view of a third embodiment of a compliant fixation device 500 of the present invention. A lead body 510 having a distal end 520 is shown. A fixation helix 530 is attached to distal end 520. Fixation helix 530 has a first end 540 and a second end 545. Second end 545 is sharpened to facilitate implantation of fixation helix 530 in a patient's cardiac tissue. In this embodiment, a piston 550 is shown disposed inside lead body 510. Piston 550 translates up and down inside lead body 510 so that fixation helix 530 can be retracted inside lead body 510 during insertion of the lead into the heart cavity. Translation of piston 550 is approximately 2 mm, the typical length of fixation helix 530. Piston 550 has a slot 555 formed therein. A stylet 565 is inserted into slot 555 to deploy fixation helix 530 for implantation into the cardiac tissue. Several methods of implantation will be discussed in further detail below.

The embodiment shown in FIG. 5 uses a ball and socket type connector. Piston 550 forms a socket 560 at its lower end 570. Piston 550 is preferably made from silicone. A ball 580, formed on first end 540 of fixation helix 530, is inserted into socket 560. In one embodiment, ball 580 is encapsulated, for example, in hydrogel for implantation. The hydrogel material is a biocompatible, bioreactive material that is used to fill a gap 590 between ball 580 and socket 560. The hydrogel prevents the ball from rotating during implantation so that torque can be effectively transferred to fixation helix 530 to screw it into the cardiac tissue. A material such as mannitol, described above, could also be used to encapsulate ball 580.

Ball 580 has a groove (not shown) formed therein to mesh with the screwdriver tip of stylet 565. To implant the helix, stylet 565 is inserted into slot 555. As stylet 565 is rotated, piston 550 and ball 580 also rotate simultaneously. Fixation helix 530 is thereby screwed into a patient's cardiac tissue. In an alternate embodiment, there is no hydrogel or other material in gap 590. Thus, ball 580 is allowed to rotate with respect to piston 550. In this embodiment, stylet 565 is used to turn only ball 580 to implant fixation helix 530. In either embodiment, stylet 565 can be reintroduced into slot 555 to unscrew fixation helix 530 for explantation.

After implantation of the lead described above in the first embodiment, the hydrogel or mannitol dissolves, thereby allowing ball 580 to rotate with respect to socket 560. A rotation of, for example, approximately 15 degrees in any direction can be achieved. This flexible design allows lead movement to be absorbed by the ball and socket configuration and not directly transferred to fixation helix 530. Because the embodiment shown in FIG. 5 provides electrically inactive fixation, an annular electrode 595 is disposed at distal end 520 of lead body 510. Electrode 595 is electrically connected to a cardiac stimulating or sensing device via a wire conductor (not shown).

Figure 6:
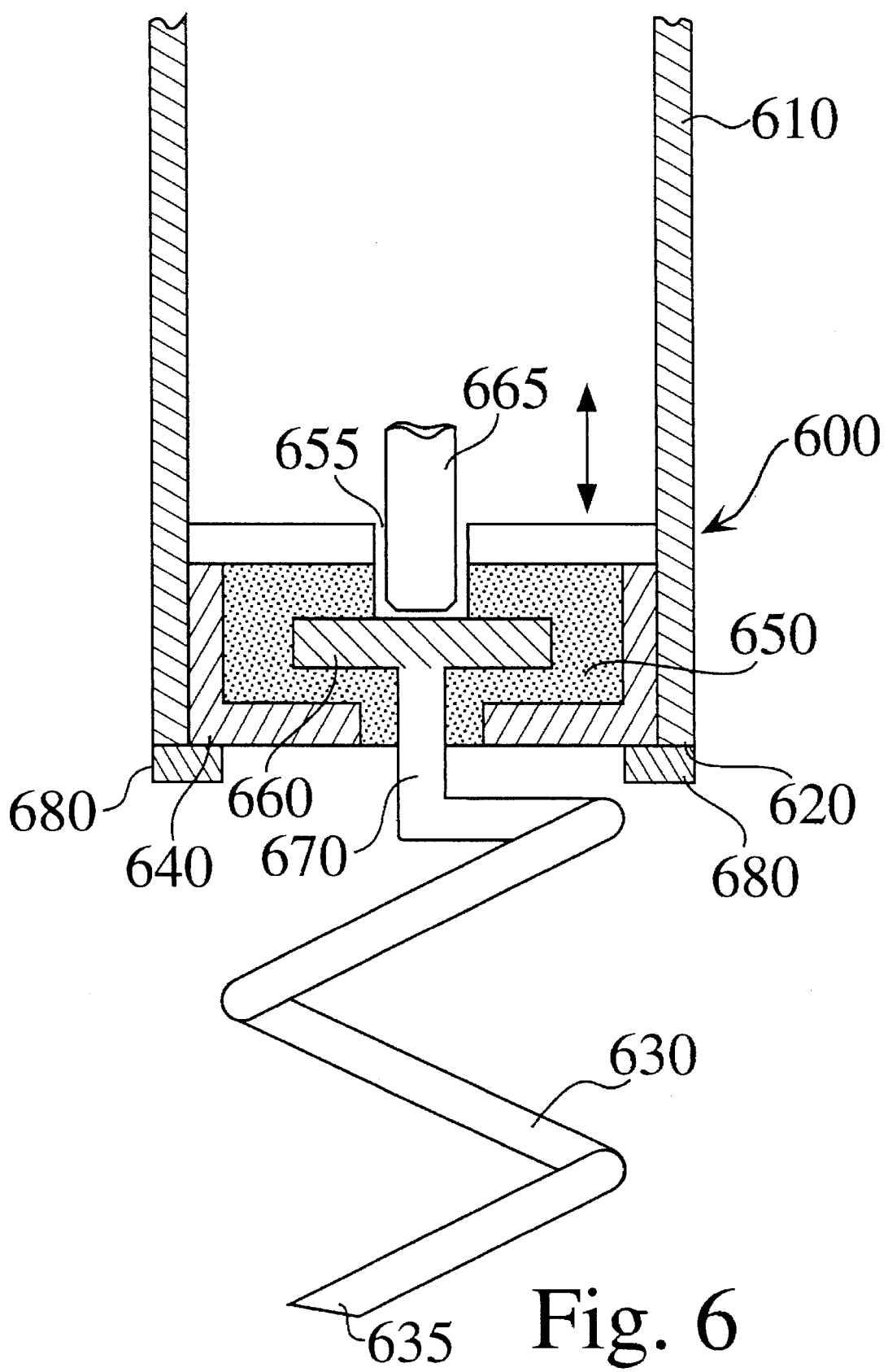
FIG. 6 is a sectional view of a fourth embodiment of a compliant fixation device of the present invention.
Figure 7:
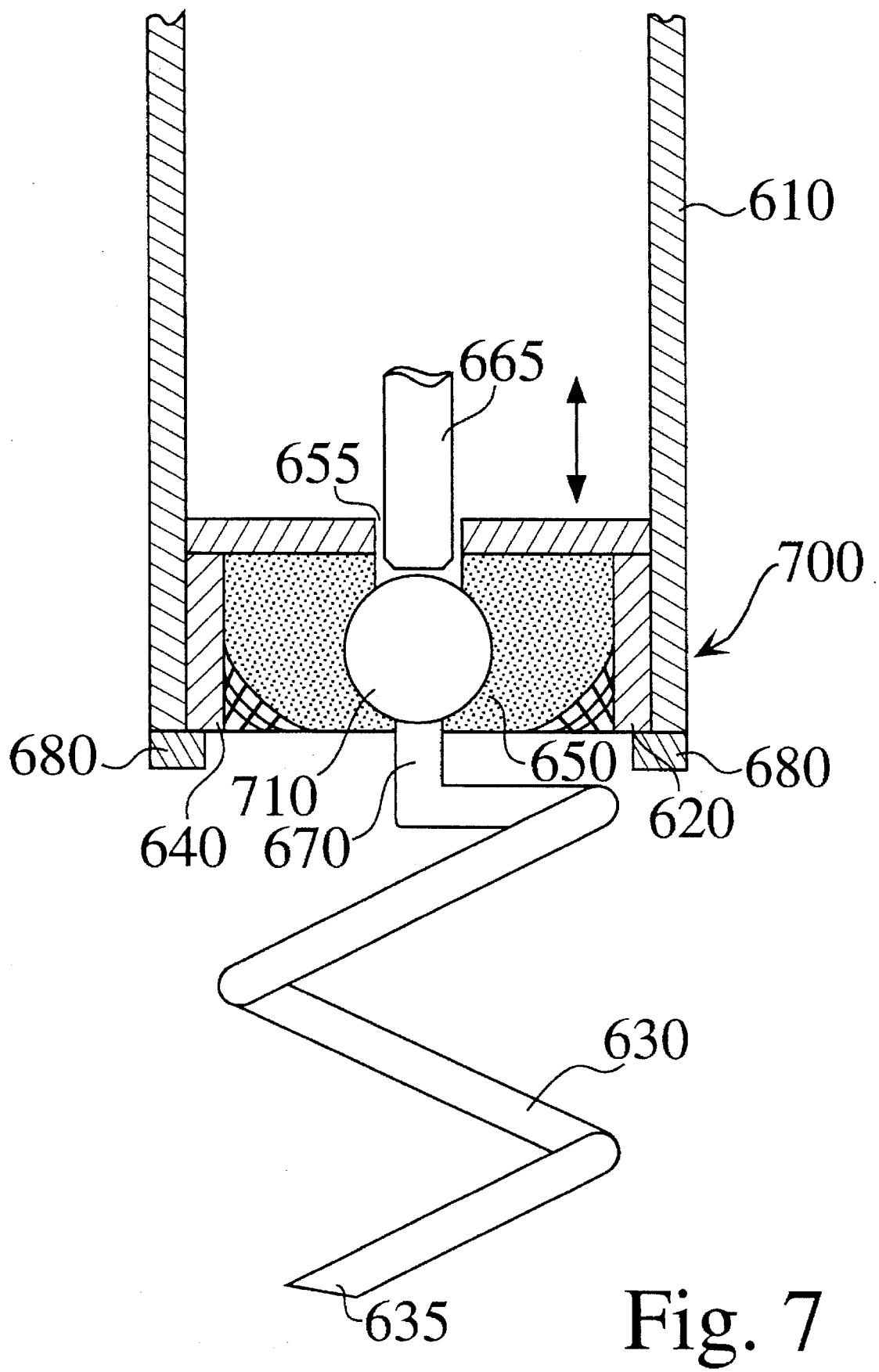
FIG. 7 is a sectional view of fifth embodiment of a compliant fixation device of the present invention.

Referring now to FIGS. 6 and 7, fourth and fifth embodiments of compliant fixation devices 600 and 700 of the present invention are shown. FIGS. 6 and 7 each show a lead body 610 having a distal end 620. A fixation helix 630 is disposed at distal end 620. Fixation helix 630 has a sharpened end 635 to facilitate implantation of the helix into a patient's cardiac tissue. Lead body 610 houses a piston chamber 640. Piston chamber 640 translates up and down within lead body 610 so that fixation helix 630 can be retracted inside lead body 610 during insertion of the lead in the heart cavity. Translation of piston chamber 640 is approximately 2 mm, the typical length of fixation helix 630.

In both embodiments, piston chamber 640 is filled with a flexible, biocompatible material 650 such as silicone rubber. Alternatively, piston chamber 640 may be filled with a biocompatible, bioreactive material, such as mannitol or PEG, so that fixation helix 630 is rigidly attached to distal end 620 of lead body 610 during insertion of the fixation helix into the patient's cardiac tissue. Once inserted, the material within piston chamber 640 dissolves, thereby allowing fixation helix 630 to freely rotate within piston chamber 640. This rotation absorbs forces from movement of lead 100 and prevents inflammation and harm to the patient's cardiac tissue surrounding the fixation helix.

Material 650 in piston chamber 640 may also be embedded with a steroid, so that as material 650 dissolves, the steroid is gradually administered to the cardiac tissue adjacent distal end 620. Application of the steroid to the cardiac tissue will prevent inflammation from occurring and will also prevent fibrous growth from occurring in the cardiac tissue surrounding fixation helix 630.

The embodiment shown in FIG. 6 has a head 660 disposed at a first end 670 of fixation helix 640. The embodiment shown in FIG. 7 has a ball 710 disposed at first end 670 of fixation helix 640. Head 660 and ball 710 are both embedded in flexible material 650, respectively, so that fixation helix 640 is flexibly attached to distal end 620 of lead body 610. Thus, forces applied to the patient's cardiac tissue by movement of the lead will be minimized.

In both embodiments, piston 650 has a slot 655 formed therein. During implantation or explantation, a stylet 665 is inserted into slot 655 such that the screwdriver tip of stylet 665 meshes with a groove (not shown) on head 660 or ball 710. Thus, as stylet 665 is rotated, piston 650 and head 660 or ball 710 also rotate. Torque is thereby effectively transferred to screw fixation helix 630 into the cardiac tissue.

Because the embodiments show in FIGS. 6 and 7 provide electrically inactive fixation, an annular electrode 680 is disposed at distal end 620 of lead body 610. Electrode 680 is electrically connected to a cardiac stimulating or sensing device via lead body 610.

Figures 8, 8A:
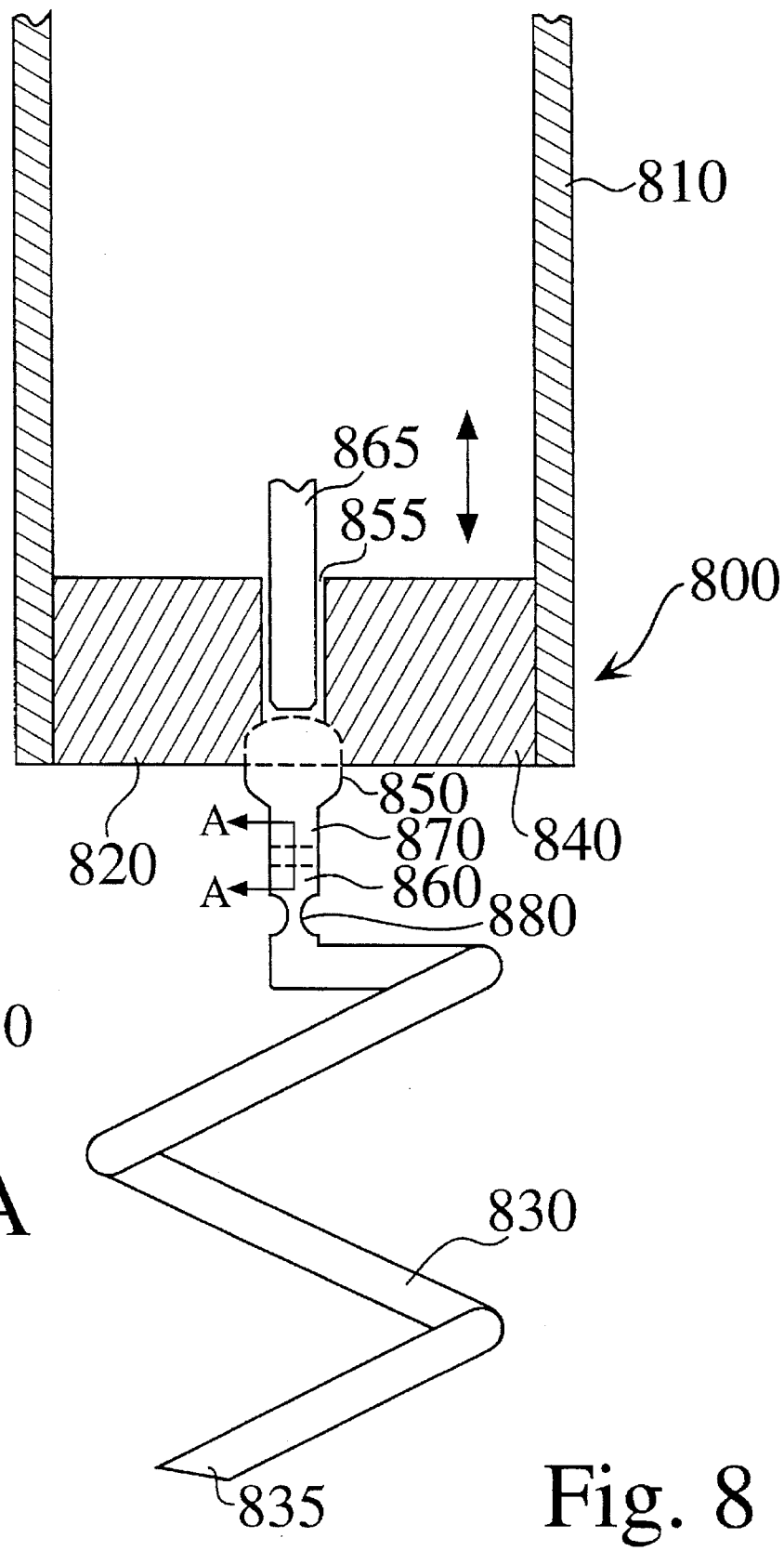
FIG. 8 is a sectional view of a sixth embodiment of a compliant fixation device of the present invention.

Referring now to FIG. 8, a sixth embodiment of a compliant fixation device 800 of the present invention is shown. FIG. 8 shows lead body 810 having a distal end 820. A fixation helix 830 is disposed at distal end 820. Fixation helix 820 has a sharpened end 835 to facilitate implantation of the helix in a patient's cardiac tissue. Lead body 810 houses a piston 840. Fixation helix 830 has a head 850 rigidly attached at a first end 860 thereof. A first thin, flattened portion 870 is shown on first end 860. As shown in FIG. 8A, first thin, flattened portion 870 flexibly bends in the transverse direction (i.e., perpendicular to the plane of the drawing sheet). A second thin, flattened portion 880 is shown on first end 860. Second thin, flattened portion 880 flexibly bends in the lateral direction (i.e., parallel to the plane of the drawing sheet). Any forces on a patient's cardiac tissue due to movement of lead body 810 are thereby minimized by the flexible connection between head 850 and fixation helix 830.

Piston 850 has a slot 855 formed therein. During implantation or explantation of fixation helix 830, a stylet 865 is inserted into slot 855. A groove (not shown) on head 850 meshes with the screwdriver tip of stylet 865 such that rotation of stylet 865 causes piston 840 and head 850 to rotate accordingly. Thus, torque from the rotation of stylet 865 is effectively transferred to implant or extract fixation helix 830 into or out of a patient's cardiac tissue.

Fixation helix 830 may be made from a flexible polymer to provide electrically inactive fixation. In the case of electrically inactive fixation, an electrode (not shown) is added to distal end 820 of lead body 810 as described above with respect to FIGS. 5–7. Alternatively, fixation helix 830 may be made from a flexible polymer with a smaller diameter core of metal in the region of flexure to provide increased flexibility and electrically active fixation.

Figure 9:
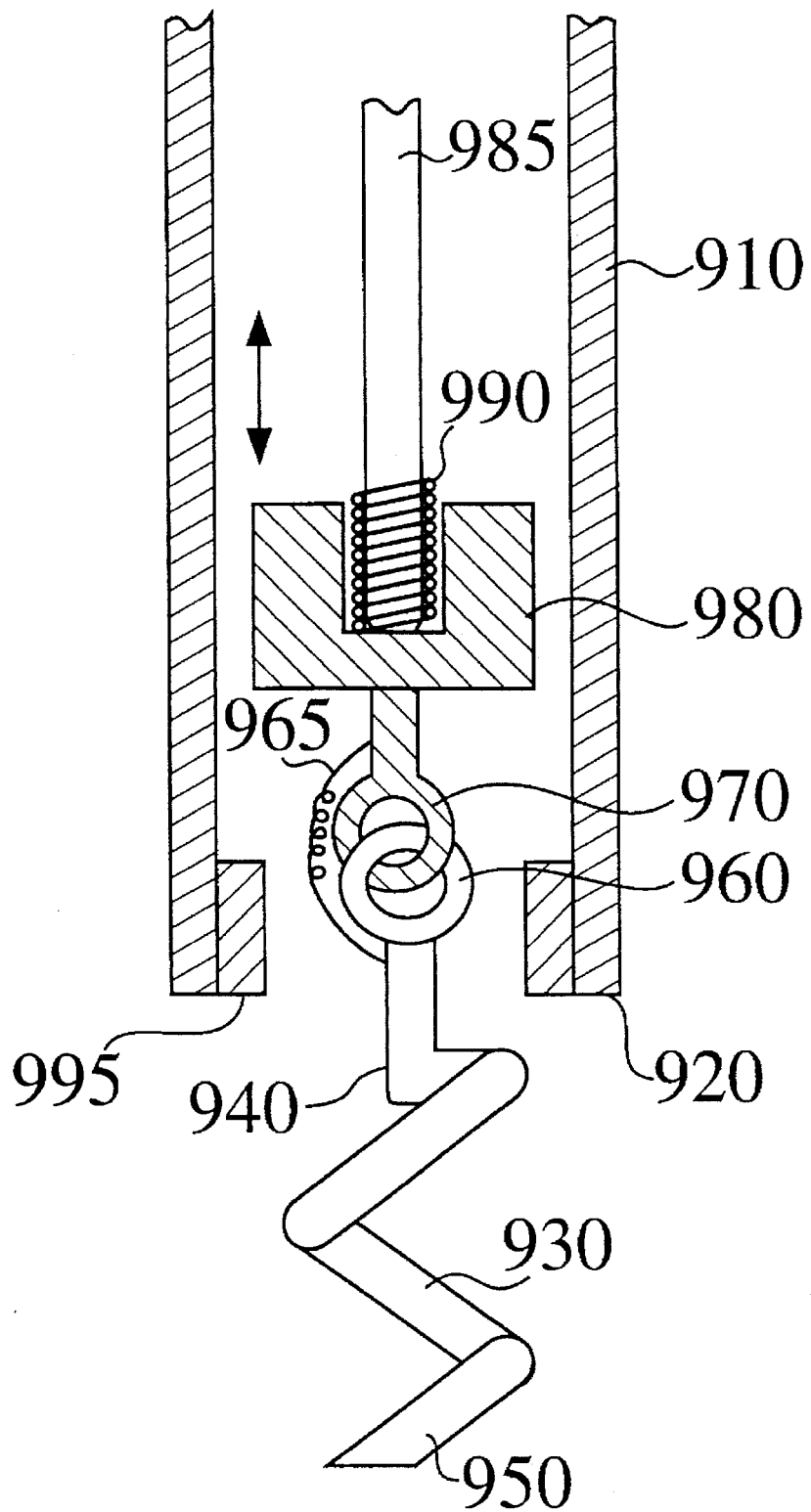
FIG. 9 is a sectional view of a seventh embodiment of a compliant fixation device of the present invention.

FIG. 9 shows a sectional view of a compliant fixation device 900 of the present invention. A lead body 910 has a distal end 920. A fixation helix 930 is disposed at distal end 920. Fixation helix 930 also translates within lead body 910 so that during implantation of the lead, fixation helix 930 can be retracted. Fixation helix 930 has a first end 940 and a second end 950. First end 940 is fixedly attached to a first annular member or ring 960. A second annular member or ring 970 is linked with first annular member 960. Second annular member 970 is also rigidly attached to a slotted end 980. Slotted end 980 is u-shaped and is configured to receive a screwdriver stylet 985. A conductor coil 990 is fixedly attached to slotted end 980 and is shown surrounding stylet 985. Conductor coil 990 provides an electrical connection between a cardiac stimulating or sensing device and fixation helix 930 to provide electrically active fixation. In this embodiment, the configuration of slotted end 980 and first and second annular members 960, 980 combine to form a universal joint.

To implant lead body 910, stylet 985 is inserted inside conductor coil 990 so that the tip of stylet 985 meshes with slotted end 980. A user then turns stylet 985 to transfer torque to slotted end 980. While annular members 960 and 970 remain within lead body 910, their movement is restricted such that torque can be efficiently transferred to fixation helix 930. This allows the user to gradually rotate fixation helix 930 to insert the helix into cardiac tissue. As fixation helix 930 is being rotated, it is also being forced outside of lead body 910. Once fixation helix 930 is fully implanted, annular members 960 and 970 will emerge from lead body 910. Without the constraints of lead body 910, annular members 960 and 970 can freely swivel about one another to provide a flexible connection between fixation helix 930 and distal end 920. Thus, movements of the patient will not be directly transferred to fixation helix 930. A stop 995 is fixedly secured to distal end 920 of lead body 910. Stop 995 prevents slotted end 980 from sliding out of lead body 910.

Fixation helix 930 is designed to provide an electrically active fixation because conductor coil 990 electrically connects fixation helix 930 to a cardiac stimulation or sensing device. Thus, one or more conductors, such as a small, flexible conductor 965, shown schematically in FIG. 9, can be attached to both annular members 960 and 970 to provide electrical continuity across the universal joint.

In an alternate embodiment, fixation helix 930 may also be designed to provide electrically inactive fixation. A separate wire connector (not shown) is inserted into lead body 910. The wire connector is connected to an electrode (not shown) at distal end 920, similar to the electrodes described above with respect to FIGS. 5–8.

Additional features may be added to any of the foregoing embodiments. For example, a fixation helix may be made from a biocompatible, porous material to enhance the sensing characteristics of the lead. In any of the embodiments, a lead may have a steroid emitted from one end to decrease the occurrence of fibroid formation. In the case of an electrically inactive fixation helix, as shown in FIGS. 6 and 7, the fixation helix may be made out of a polymer to enhance the flexibility of the distal end of the lead body. In the case of an electrically active fixation helix, the fixation helix may be made from a polymer, where the polymer surrounds a thin metal conductor. Thus, the fixation helix could be electrically connected to the cardiac stimulation device and also achieve an added degree of flexibility.

While the invention has been particularly shown and described with reference to preferred embodiments thereof, it will be understood by those skilled in the art that various changes in form and details may be made therein without departing from the spirit and scope of the invention.

What is claimed is:

1. A compliant fixation mechanism connected to a lead for flexibly securing the lead to a patient's cardiac tissue, comprising:

a fixation helix; and a flexible connector attached between said fixation helix and said lead, said flexible connector reducing forces transferred between said fixation helix and said lead, wherein said lead has a distal end and wherein said flexible connector comprises:

joint means for flexibly attaching said fixation helix to said distal end of the lead; and bioreactive material surrounding said joint means to hold said joint means rigid during securing of said fixation helix to the cardiac tissue, wherein said bioreactive material reacts after implantation of the lead to permit said decoupling to occur.

2. The compliant fixation mechanism of claim 1, wherein said joint means comprises a coil spring.

3. The compliant fixation mechanism of claim 1, wherein said joint means comprises a flexible silicone rod.

4. The compliant fixation mechanism of claim 3, further comprising:

a conductor coil embedded in said flexible silicone rod to provide an electrically conductive path between said fixation helix and the lead.

5. The compliant fixation mechanism of claim 1, wherein said joint means comprises:

a piston disposed in the distal end of the lead, said piston being longitudinally translatable within the lead and having a socket therein;

a ball rigidly attached to a first end of said fixation helix and disposed within said socket; and wherein said bioreactive material is disposed between said ball and said socket to rigidly fix said ball in said socket for implantation of said fixation helix in cardiac tissue, and whereby said bioreactive material dissolves after implantation of said fixation helix to permit rotation of said ball within said socket.

6. An intracardiac lead for transvenous implantation within a patient's heart having cardiac tissue, comprising:

an electrode tip for delivering electrical energy to the patient's heart, said electrode tip including means for securing said electrode tip to tissue within the patient's heart;

a lead body for delivering electrical energy to said electrode tip; and a flexible connector attached between said securing means and said lead body, said flexible connector reducing forces transferred between said lead body and said securing means, wherein said flexible connector comprises:

joint means for flexibly attaching said securing means to the lead; and bioreactive material surrounding said joint means to hold said joint means rigid during implantation of said securing means in cardiac tissue, wherein said bioreactive material reacts after implantation of said securing means to permit said decoupling to occur.

7. The intracardiac lead of claim 6, wherein said joint means comprises a coil spring.

8. The intracardiac lead of claim 6, wherein said joint means comprises a flexible silicone rod.

9. The intracardiac lead of claim 8, further comprising:

a conductor coil embedded in said flexible silicone rod to provide an electrically conductive path between said securing means and the lead.

10. The intracardiac lead of claim 6, wherein said joint means comprises:

a piston disposed in the distal end of the lead, said piston being longitudinally translatable within the lead and having a socket therein;

a ball rigidly attached to a first end of said securing means and disposed within said socket; and wherein said bioreactive material is disposed between said ball and said socket to rigidly fix said ball in said socket for implantation of said securing means in cardiac tissue, and whereby said bioreactive material dissolves after implantation of said securing means to permit rotation of said ball within said socket.

11. An intracardiac lead for transvenous implantation within a patient's heart having cardiac tissue, comprising:

and electrode tip for delivering electrical energy to the patient's heart, said electrode tip including a fixation helix for securing said electrode tip to tissue within the patient's heart;

a lead body for delivering electrical energy to said electrode tip;

a coil spring for flexibly attaching said fixation helix to a distal end of the lead and for decoupling lateral forces on said lead body from being transferred to said electrode tip; and bioreactive material surrounding said spring to hold said spring in a rigid state during implantation of said electrode tip in the cardiac tissue, wherein said bioreactive material reacts after implantation of the lead to permit said decoupling to occur.

* * * * *